US007753892B2

(12) United States Patent
Newton et al.

(10) Patent No.: US 7,753,892 B2
(45) Date of Patent: Jul. 13, 2010

(54) ANTI-DRAWBACK MEDICAL VALVE (75) Inventors: Brian L. Newton, Woonsocket, RI (US); Andrew L. Cote, Sr., Merrimack, NH (US); Charles F. Ganem, Cape Neddick, ME (US)

(73) Assignee: Nypro Inc., Clinton, MA (US)

( * ) Notice: Subject to any disclaimer, the term of this patent is extended or adjusted under 35 U.S.C. 154(b) by 1293 days.

(21) Appl. No.: 11/058,381

(22) Filed: Feb. 15, 2005

(65) Prior Publication Data
US 2005/0165365 A1    Jul. 28, 2005

Related U.S. Application Data (63) Continuation-in-part of application No. 10/291,448, filed on Nov. 7, 2002, now Pat. No. 6,869,426.

(60) Provisional application No. 60/350,738, filed on Nov. 13, 2001, provisional application No. 60/645,644, filed on Jan. 21, 2005.

(51) Int. Cl.
*A61M 5/315* (2006.01)
*A61M 5/00* (2006.01)
*A61M 25/00* (2006.01)
*E03B 1/00* (2006.01)
*F17D 1/00* (2006.01)
*F17D 3/00* (2006.01)
*F16L 37/32* (2006.01)

(52) U.S. Cl. .................. 604/236; 604/246; 604/523; 137/614.04; 137/1

(58) Field of Classification Search .............. 604/533, 604/246–256, 167.01–167.05, 200–202, 604/905; 251/149.1
See application file for complete search history.

(56) References Cited

U.S. PATENT DOCUMENTS

| 2,594,405 A | 4/1952 | Deters |
| 2,693,801 A | 11/1954 | Foreman |
| 2,705,501 A | 4/1955 | Frizsch et al. |
| 2,756,740 A | 7/1956 | Deane |

(Continued)

FOREIGN PATENT DOCUMENTS

EP    0268480 A1    5/1988

(Continued)

OTHER PUBLICATIONS

Authorized Officer Peggy Prenzel, *The International Search Report and The Written Opinion of the International Searching Authority*, International Searching Authority, Jul. 10, 2005, 12 pages.

*Primary Examiner*—Nicholas D Lucchesi
*Assistant Examiner*—Ian K Holloway
(74) *Attorney, Agent, or Firm*—Sunstein Kann Murphy & Timbers LLP (57) ABSTRACT

A medical valve has an interior flow path having a volume that is substantially the same when in either the closed mode (when the valve is closed) or the open mode (when the valve is open). To those ends, the medical valve has a housing forming an interior, and a valve mechanism (within the interior) having a substantially rigid translating member with a bore. The interior of the housing has a flow path that includes at least a portion of the bore of the translating member. As noted above, the open mode volume is substantially equal to the closed mode volume.

50 Claims, 8 Drawing Sheets

U.S. PATENT DOCUMENTS

| | | |
|---|---|---|
| 2,899,975 A | 8/1959 | Fernandez |
| 2,999,499 A | 9/1961 | Willett |
| 3,087,492 A | 4/1963 | Garth |
| 3,105,511 A | 10/1963 | Murphy, Jr. |
| 3,192,949 A | 7/1965 | De See |
| 3,385,301 A | 5/1968 | Harautuneian |
| 3,399,677 A | 9/1968 | Gould et al. |
| 3,416,567 A | 12/1968 | Von Dardel et al. |
| 3,506,005 A | 4/1970 | Gilio et al. |
| 3,538,950 A | 11/1970 | Porteners |
| 3,570,484 A | 3/1971 | Steer |
| 3,572,375 A | 3/1971 | Rosenberg |
| 3,726,282 A | 4/1973 | Patel |
| 3,806,086 A | 4/1974 | Cloyd |
| 3,831,629 A | 8/1974 | Mackal et al. |
| 3,838,843 A | 10/1974 | Bernhard |
| 3,923,065 A | 12/1975 | Nozick et al. |
| 3,965,910 A | 6/1976 | Fischer |
| 3,994,293 A | 11/1976 | Ferro |
| 4,063,555 A | 12/1977 | Ulinder |
| 4,080,965 A | 3/1978 | Phillips |
| 4,094,195 A | 6/1978 | Friswell et al. |
| 4,094,196 A | 6/1978 | Friswell |
| 4,116,201 A | 9/1978 | Shah |
| 4,121,585 A | 10/1978 | Becker, Jr. |
| 4,143,853 A | 3/1979 | Abramson |
| 4,223,808 A | 9/1980 | Williams et al. |
| 4,300,571 A | 11/1981 | Waldbillig |
| 4,324,239 A * | 4/1982 | Gordon et al. ............... 604/122 |
| 4,333,455 A | 6/1982 | Bodicky |
| 4,334,551 A | 6/1982 | Pfister |
| 4,344,435 A | 8/1982 | Aubin |
| 4,387,879 A | 6/1983 | Tauschinski |
| 4,401,432 A | 8/1983 | Schwartz |
| 4,421,296 A | 12/1983 | Stephens |
| 4,458,480 A | 7/1984 | Irwin |
| 4,496,348 A | 1/1985 | Genese et al. |
| 4,498,658 A | 2/1985 | Mikiya |
| 4,534,758 A | 8/1985 | Akers et al. |
| 4,535,820 A | 8/1985 | Raines |
| 4,550,785 A | 11/1985 | Hibbard et al. |
| 4,551,136 A | 11/1985 | Mandl |
| 4,585,435 A | 4/1986 | Vaillancourt |
| 4,596,557 A | 6/1986 | Pexa |
| 4,611,973 A | 9/1986 | Birdwell |
| 4,617,015 A | 10/1986 | Foltz |
| 4,661,110 A | 4/1987 | Fortier et al. |
| 4,675,003 A | 6/1987 | Hooven |
| 4,681,132 A | 7/1987 | Lardner |
| 4,683,905 A | 8/1987 | Vigneau et al. |
| 4,683,916 A | 8/1987 | Raines |
| 4,698,061 A | 10/1987 | Makaryk et al. |
| 4,710,168 A | 12/1987 | Schwab et al. |
| 4,712,583 A | 12/1987 | Pelmulder et al. |
| 4,743,235 A | 5/1988 | Waldbillig et al. |
| 4,745,950 A | 5/1988 | Mathieu |
| 4,749,003 A | 6/1988 | Leason |
| 4,752,287 A | 6/1988 | Kurtz et al. |
| 4,752,292 A | 6/1988 | Lopez et al. |
| 4,758,224 A | 7/1988 | Siposs |
| 4,776,369 A | 10/1988 | Lardner et al. |
| 4,809,679 A | 3/1989 | Shimonaka et al. |
| 4,816,020 A | 3/1989 | Brownell |
| 4,819,684 A | 4/1989 | Zaugg et al. |
| 4,830,331 A * | 5/1989 | Vindum ....................... 251/63 |
| 4,850,978 A | 7/1989 | Dudar et al. |
| 4,874,377 A | 10/1989 | Newgard et al. |
| 4,915,687 A | 4/1990 | Sivert |
| 4,917,668 A | 4/1990 | Haindl |
| 4,935,010 A | 6/1990 | Cox et al. |
| 4,966,199 A | 10/1990 | Ruschke |
| 5,006,114 A | 4/1991 | Rogers et al. |
| 5,041,087 A | 8/1991 | Loo et al. |
| 5,048,537 A | 9/1991 | Messinger |
| 5,049,128 A | 9/1991 | Duquette |
| 5,059,175 A | 10/1991 | Hanover et al. |
| 5,065,783 A | 11/1991 | Ogle, II |
| 5,080,654 A | 1/1992 | Picha et al. |
| 5,085,645 A | 2/1992 | Purdy et al. |
| 5,100,394 A | 3/1992 | Dudar et al. |
| 5,108,380 A | 4/1992 | Herlitze et al. |
| 5,147,333 A | 9/1992 | Raines |
| 5,171,230 A | 12/1992 | Eland et al. |
| 5,184,652 A | 2/1993 | Fan ............................ 141/21 |
| 5,199,947 A | 4/1993 | Lopez et al. |
| 5,201,715 A | 4/1993 | Masters |
| 5,203,775 A | 4/1993 | Frank et al. |
| 5,215,538 A | 6/1993 | Larkin |
| 5,221,271 A | 6/1993 | Nicholson et al. |
| 5,230,706 A | 7/1993 | Duquette |
| 5,242,393 A | 9/1993 | Brimhall et al. |
| 5,242,432 A | 9/1993 | DeFrank |
| 5,269,771 A | 12/1993 | Thomas et al. |
| 5,280,876 A | 1/1994 | Atkins |
| 5,300,034 A | 4/1994 | Behnke et al. |
| 5,320,328 A | 6/1994 | Decloux et al. |
| 5,330,435 A | 7/1994 | Vaillancourt |
| 5,349,984 A | 9/1994 | Weinheimer et al. |
| 5,360,413 A | 11/1994 | Leason et al. |
| 5,380,306 A | 1/1995 | Brinon |
| 5,390,898 A | 2/1995 | Smedley et al. |
| 5,401,255 A | 3/1995 | Sutherland et al. |
| 5,439,451 A | 8/1995 | Collinson et al. |
| 5,465,938 A | 11/1995 | Werge et al. |
| 5,474,536 A | 12/1995 | Bonaldo |
| 5,474,544 A | 12/1995 | Lynn |
| 5,509,433 A | 4/1996 | Paradis |
| 5,509,912 A | 4/1996 | Vaillancourt et al. |
| 5,520,666 A | 5/1996 | Choudhury et al. |
| 5,533,708 A | 7/1996 | Atkinson et al. |
| 5,533,983 A | 7/1996 | Haining |
| 5,549,566 A | 8/1996 | Elias et al. |
| 5,569,209 A | 10/1996 | Roitman |
| 5,569,235 A | 10/1996 | Ross et al. |
| 5,573,516 A | 11/1996 | Tyner |
| 5,578,059 A | 11/1996 | Patzer |
| 5,616,129 A | 4/1997 | Mayer |
| 5,616,130 A | 4/1997 | Mayer |
| 5,620,434 A | 4/1997 | Brony |
| 5,674,206 A | 10/1997 | Allton et al. |
| 5,676,346 A | 10/1997 | Leinsing |
| 5,685,866 A | 11/1997 | Lopez |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,730,418 A | 3/1998 | Feith et al. |
| 5,749,861 A | 5/1998 | Guala et al. |
| RE35,841 E | 7/1998 | Frank et al. |
| 5,806,831 A | 9/1998 | Paradis |
| 5,820,601 A | 10/1998 | Mayer |
| 5,921,264 A | 7/1999 | Paradis |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,068,011 A | 5/2000 | Paradis |
| 6,079,432 A | 6/2000 | Paradis |
| 6,089,541 A | 7/2000 | Weinheimer et al. |
| 6,152,900 A | 11/2000 | Mayer |
| 6,228,069 B1 | 5/2001 | Barth et al. |
| 6,245,048 B1 | 6/2001 | Fangrow, Jr. et al. |

| | | |
|---|---|---|
| 6,290,206 B1 | 9/2001 | Doyle |
| 6,325,099 B1 * | 12/2001 | Bunschoten et al. ... 137/614.04 |
| 6,344,033 B1 | 2/2002 | Jepson et al. |
| 6,428,520 B1 | 8/2002 | Lopez et al. |
| 6,482,188 B1 | 11/2002 | Rogers et al. ............ 604/249 |
| 6,543,745 B1 | 4/2003 | Enerson |
| 6,581,906 B2 * | 6/2003 | Pott et al. ............... 251/149.1 |
| 6,595,964 B2 | 7/2003 | Finley et al. |
| 6,595,981 B2 * | 7/2003 | Huet ........................ 604/523 |
| 6,609,696 B2 | 8/2003 | Enerson |
| 6,669,673 B2 | 12/2003 | Lopez |
| 6,745,998 B2 * | 6/2004 | Doyle ..................... 251/149.6 |
| 6,755,391 B2 | 6/2004 | Newton et al. .......... 251/149.6 |
| 6,883,778 B1 * | 4/2005 | Newton et al. .......... 251/149.1 |
| 7,037,302 B2 | 5/2006 | Vaillancourt ............. 604/533 |
| 2003/0050610 A1 * | 3/2003 | Newton et al. ........... 604/256 |
| 2003/0093061 A1 | 5/2003 | Ganem |
| 2003/0098430 A1 | 5/2003 | Leinsing et al. |
| 2003/0141477 A1 | 7/2003 | Miller |
| 2004/0073171 A1 | 4/2004 | Rogers et al. |
| 2004/0206924 A1 * | 10/2004 | Newton et al. .......... 251/149.1 |
| 2007/0218757 A1 | 9/2007 | Guala ....................... 439/589 |
| 2008/0190485 A1 * | 8/2008 | Guala ........................... 137/1 |
| 2008/0275405 A1 | 11/2008 | Newton et al. ............. 604/256 |

FOREIGN PATENT DOCUMENTS

| | | |
|---|---|---|
| EP | 0629418 A1 | 12/1994 |
| EP | 1243285 | 9/2002 |
| GB | 2079162 | 1/1982 |
| WO | WO 83/02559 | 8/1983 |
| WO | WO 93/11828 | 6/1993 |
| WO | WO 96/00107 | 1/1996 |
| WO | WO 97/39791 | 10/1997 |
| WO | WO 98/22178 | 5/1998 |
| WO | WO 98/26835 | 6/1998 |
| WO | WO 98/39594 | 9/1998 |
| WO | WO 00/44433 | 8/2000 |
| WO | WO 01/20218 A1 | 3/2001 |
| WO | WO 03/018104 A2 | 3/2003 |
| WO | WO 03/018105 A1 | 3/2003 |
| WO | WO 2004/060466 | 7/2004 |

* cited by examiner

ANTI-DRAWBACK MEDICAL VALVE

PRIORITY

This patent application claims priority from and is a continuation-in-part of U.S. patent application Ser. No. 10/291,448, filed Nov. 7, 2002, entitled, "ANTI-DRAWBACK MEDICAL VALVE," and naming Charles F. Ganem as inventor, the disclosure of which is incorporated herein, in its entirety, by reference. As a result of the priority claim, this patent application also claims priority from provisional U.S. Patent Application No. 60/350,738, filed Nov. 13, 2001, the disclosure of which also is incorporated herein, and its entirety, by reference.

This patent application also claims priority from Provisional U.S. Patent Application No. 60/645,644, filed Jan. 21, 2005, entitled, "ANTI-DRAWBACK MEDICAL VALVE," assigned to Nypro Inc. of Clinton, Mass., and naming Brian L. Newton and Andrew L. Cote, Sr. as inventors, the disclosure of which is incorporated herein, in its entirety, by reference.

FIELD OF THE INVENTION

The invention generally relates to medical valves and, more particularly, the invention relates to medical valves that substantially eliminate fluid drawback.

BACKGROUND OF THE INVENTION

In general terms, medical valving devices often act as a sealed port that may be repeatedly accessed to non-invasively inject fluid into (or withdraw fluid from) a patient's vasculature. Consequently, a medical valve permits the patient's vasculature to be freely accessed without requiring such patient's skin be repeatedly pierced by a needle.

Medical personnel insert a syringe into the proximal port of a properly secured medical valve to inject fluid into (or withdraw fluid from) a patient. Once inserted, the syringe may freely inject or withdraw fluid to and from the patient. Problems arise, however, when the syringe is withdrawn from many different types of prior art valves. Specifically, a back pressure (i.e., a proximally directed pressure) produced by the withdrawing syringe undesirably can cause blood to be drawn proximally into a catheter attached to the valve, or into the valve itself. In addition to coagulating and impeding the mechanical operation of the valve, blood in the catheter or valve also compromises sterility.

SUMMARY OF THE INVENTION

In accordance with one aspect of the invention, a medical valve has an interior flow path having a volume that is substantially the same when in either the closed mode (when the valve is closed) or the open mode (when the valve is open). To those ends, the medical valve has a housing forming an interior, and a valve mechanism (within the interior) having a substantially rigid translating member with a bore. The interior of the housing has a flow path that includes at least a portion of the bore of the translating member. As noted above, the open mode volume is substantially equal to the closed mode volume.

In some embodiments, the flow path has a volume that remains substantially constant as the valve transitions between the open mode and the closed mode. Moreover, the flow path may have at least a portion of the bore and a second portion. In that and other cases, the translating member may extend through the second portion of the flow path. The second portion also may have a substantially constant volume as the valve transitions between modes.

The interior also may include a receiving chamber that is outside of the flow path. The translating member illustratively extends into the receiving chamber when the valve is in the closed mode. In addition, the translating member may have a substantially static shape as the valve transitions between the open mode and the closed mode.

In illustrative embodiments, the valve substantially has neither a positive push nor a drawback when the valve transitions from the open mode to the closed mode. In a similar manner, the valve may substantially have neither a positive push bolus nor a drawback bolus when the valve transitions from the closed mode to the open mode. Moreover, movement of the translating member may cause substantially no volumetric change within any part of the flow path when the valve transitions between the open and closed modes.

Among other things, the translating member includes a cannula or a tube. In yet other embodiments, the valve mechanism has a proximal section and the housing also has a distal port. In that and other cases, the flow path may extend from the proximal section of the valve mechanism to the distal port.

In accordance with another aspect of the invention, a medical valve has a housing forming an interior having a proximal port and a distal port, and the interior forms a flow path between the proximal port and the distal port. The valve also has a translating member (having a bore) that is longitudinally movable within the interior. The flow path includes the bore and a second portion that is bounded by the translating member. The flow path maintains a substantially constant volume when the valve transitions between the open mode and the closed mode.

The second portion preferably remains substantially stationary within the interior when the valve transitions between the open and closed modes. In addition, the bore may maintain a substantially constant volume between the open and closed modes. The valve also may have an elastomeric member (within the interior) that prevents fluid flow through the bore when the valve is in the closed mode. In this and other cases, the bore may have at least two longitudinally spaced openings normally occluded by the elastomeric member when the valve is in the closed mode.

In some embodiments, the valve also has a valve mechanism that includes the translating member and the elastomeric member. The valve mechanism may be substantially flush with or extends proximally from the proximal port when the valve is in the closed mode. Other embodiments configure the second portion of the flow path to have a part with a first boundary and a second boundary. In that and other cases, the translating member may extend at least from the first boundary to the second boundary. Moreover, the translating member may bound the second portion of the flow path in both the closed mode and in the open mode.

In accordance with another aspect of the invention, a medical valve has a housing having a distal port and an interior, and a valve mechanism within the interior. The valve mechanism has a sealing member, while the interior has components forming a flow path extending from the sealing member and terminating at the distal port. The sealing member cooperates with at least one of the components to selectively open and close the valve. The components each maintain substantially constant shapes as the valve transitions between the open mode and the closed mode. The distal port substantially has neither a positive push nor a drawback when the valve transitions from the open mode to the closed mode.

In accordance with another aspect of the invention, a method of controlling fluid flow through a valve forms a flow path within the valve interior. The formed flow path has a first portion and a second portion. The method longitudinally moves the first portion relative to the second portion to change the mode of the valve. Each of the first portion and the second portion has a substantially static shape when the valve transitions between the open mode and the closed mode.

BRIEF DESCRIPTION OF THE DRAWINGS

The foregoing and advantages of the invention will be appreciated more fully from the following further description thereof with reference to the accompanying drawings wherein.

DESCRIPTION OF ILLUSTRATIVE EMBODIMENTS

In illustrative embodiments, a medical valve substantially has neither a positive push nor a drawback at any point in its opening or closing stroke. To those ends, such a valve illustratively has a flow path that maintains a substantially static shape and thus, a substantially constant volume, throughout the opening or closing stroke. Details of illustrative embodiments are discussed below.

Figure 1:
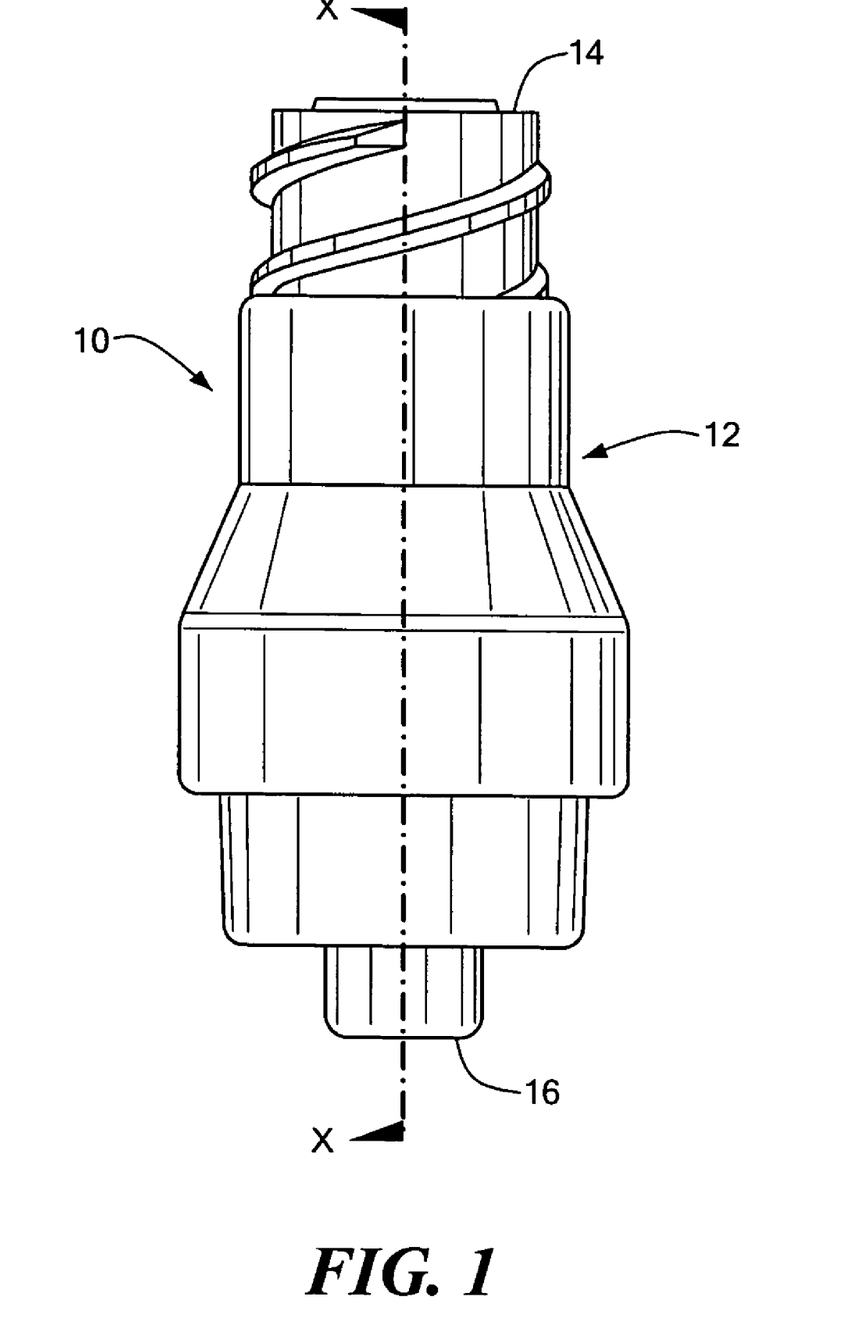
FIG. 1 schematically shows a medical valve that may be configured in accordance with illustrative embodiments of the invention.

FIG. 1 schematically shows a medical valve 10 that may be configured to substantially eliminate fluid drawback (a/k/a "back-flow") while a syringe or other type of nozzle is connecting to or withdrawing from it. The valve 10 has a valve housing 12 forming an interior 13 having proximal and distal ports 14 and 16 (also respectively referred to herein as "inlet 14" and "outlet 16"). The interior 13 contains a valve mechanism (various embodiments of the valve mechanism are shown in the subsequent figures) that controls fluid flow through the valve 10. The fluid preferably is in liquid form, such as saline or a liquid medication, to pass through a fluid path that extends between the inlet 14 and the outlet 16. Although much of the discussion herein refers to the proximal port 14 as a fluid inlet, and the distal port 16 as a fluid outlet, the proximal and distal ports 14 and 16 also may be respectively used as outlet and inlet ports.

As discussed below, the valve 10 has components that are similar to the luer-activated swab valve disclosed in U.S. Pat. No. 6,039,302 entitled, "SWABBABLE LUER-ACTIVATED VALVE," the disclosure of which is incorporated herein, in its entirety, by reference. Of course, various embodiments may relate to other types of valves and thus, such embodiments are not limited to swab valves and/or luer-activated valves. Other embodiments are related to valves shown in the pending U.S. patent application Ser. Nos. 09/479,327 and 09/812,237, the disclosures of which are incorporated herein, in their entireties, by reference.

Figure 2:
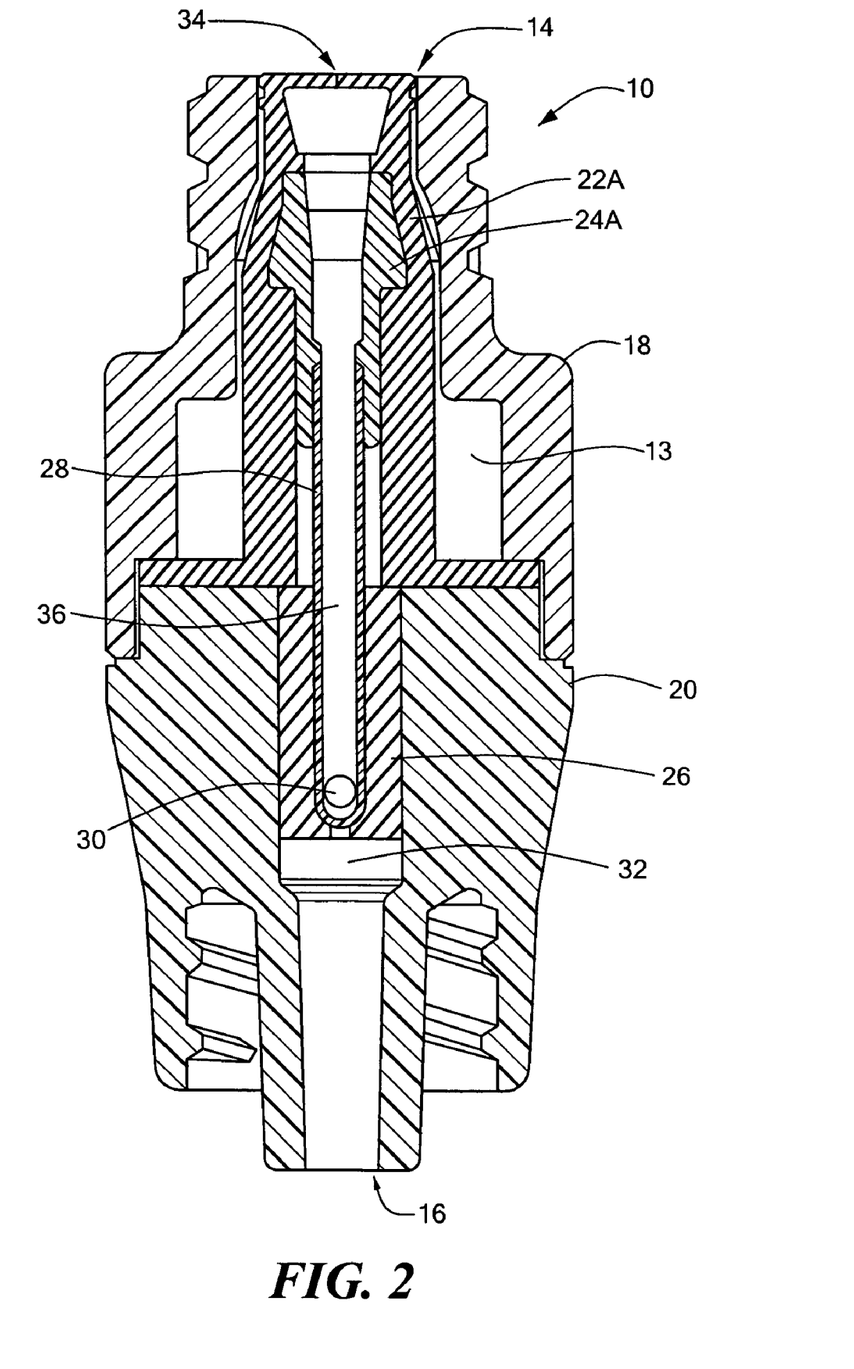
FIG. 2 schematically shows a cross-sectional view of the medical valve shown in FIG. 1 configured in accordance with one embodiment of the invention.

FIG. 2 schematically shows a cross-sectional view along line X-X of one embodiment of the valve 10 shown in FIG. 1. The housing 12 includes inlet and outlet housing portions 18 and 20, which illustratively are formed from a hard plastic material (e.g., polycarbonate, polypropylene, or polyethylene) that are snap-fit together. For example, the housing portions 18 and 20 may be configured to snap fit together in accordance with the teachings of co-pending, commonly owned U.S. patent application Ser. No. 10/265,292, filed Oct. 4, 2002, the disclosure of which is incorporated herein, in its entirety, by reference. It should be noted that although some embodiments are discussed as being snap-fit components, various embodiments of the invention may be coupled by either snap-fit or other means, such as by ultrasonic welding. Accordingly, such embodiments are not intended to be limited to snap-fit components.

When coupled, the housing portions 18 and 20 form the interior 13, which is shaped to comply with the operation of its internal valve element (discussed below) that selectively permits fluid flow. The proximal port 14, which is part of the interior 13, illustratively is contoured to accept various types of nozzles, such as those complying with ANSI/ISO standards (e.g., luers complying with ANSI and/or ISO standards).

The valve mechanism includes a stretchable and compressible gland 22A secured between the inlet housing portion 18 and outlet housing portion 20, a rigid and longitudinally movable cannula 24A secured within the valve 10 by the gland 22A, and a membrane 26 to partially occlude fluid flow from the cannula 24A.

The cannula 24A includes a proximal section that is coupled with a distally located thin section. In illustrative embodiments, the thin section is a hollow needle (identified by reference number "28") that, together with the proximal section, forms a flow path (referred to below as a "bore" and identified by reference number 36). The needle 28 is open at its proximal end, closed at its distal end, and has a hole 30 in its side just proximal to its distal end. When in the closed position (i.e., the "closed mode," which prevents fluid flow through the valve 10), the hole 30 is occluded by the membrane 26, which is held fixed between outlet housing portion 20 and the gland 22A.

The outlet housing portion 20 forms a chamber 32 (within the housing interior 13) having a volume that, in some embodiments, changes slightly as the needle 28 is urged proximally and distally by a nozzle. In one embodiment, the volume of the chamber 32 is slightly greater when in the closed mode than when in the open mode. This slight difference in volume is due to the volume of the needle 28 extending into the chamber 32.

Insertion of a nozzle against a slit 34 at the proximal end of the gland causes the cannula 24A to move distally, thereby moving the hole 30 from its occluding contact with the membrane 26. Liquid consequently may be directed first through the cannula flow path and hole 30, then through the chamber 32, and out of the valve 10 through the distal port 16.

In an illustrative embodiment of the invention, the needle 28 is sized to be very thin. The amount of fluid drawn back into the chamber 32 as the nozzle is withdrawn corresponds to the volume of the needle 28 required to expose the hole 30 to the chamber 32. Consequently, as suggested above, this volume is controlled by the needle diameter and the placement of the hole 30. By making the diameter of the needle 28 small and the hole 30 very close to the distal end of the needle 28, the volume of fluid drawn back into the chamber 32 is reduced and the subsequent risk from contamination to the valve 10 minimized. In certain embodiments, the volume of fluid drawn back upon withdrawal of the nozzle is on the order of between about one and several microliters. In some embodiments, the total volume of fluid drawn back is on the order of about 0.5 microliters.

In some embodiments, a bump or other type of protrusion can be included on the needle 28 to pull (i.e., stretch) the membrane 26 back beyond its normally neutral position. In so doing, the membrane 26 is pulled to a point at which the membrane 26 will be released from the bump on the needle 28. As the membrane 26 returns to its neutral position, it pushes fluid forward through the outlet (referred to herein as "positive push"). In still other embodiments, the bump may be a part of the membrane 26.

It is contemplated that the amount of fluid pushed forward/distally by this bump can be controlled to cancel out with the amount of drawback caused by the needle 28 returning into the membrane 26. In other words, the volume of the internal chamber 32 remains substantially constant as the valve 10 transitions between the open and closed modes. When this occurs, a meniscus at the distal port 16 (when the distal port 16, or end of a catheter to which it is attached, is facing upwardly) will be substantially unchanged as the nozzle is withdrawn from the valve 10.

Accordingly, in this case, the valve 10 has neither a positive push nor a drawback when the it transitions from the open mode to the closed mode. In practice, this embodiment can have negligible amounts in either direction (e.g., less then one microliter). This design, which has insubstantial/negligible drawback and/or positive push, thus may be considered to have a "neutral" drawback.

In illustrative embodiments, the distal end of the needle 28 is bulbous to facilitate its movement through the membrane 26. In such embodiment, the hole 30 is located immediately above the bulbous distal end. In other embodiments, the membrane 26 and gland 22A are a single unitary molded part.

Figure 3A:
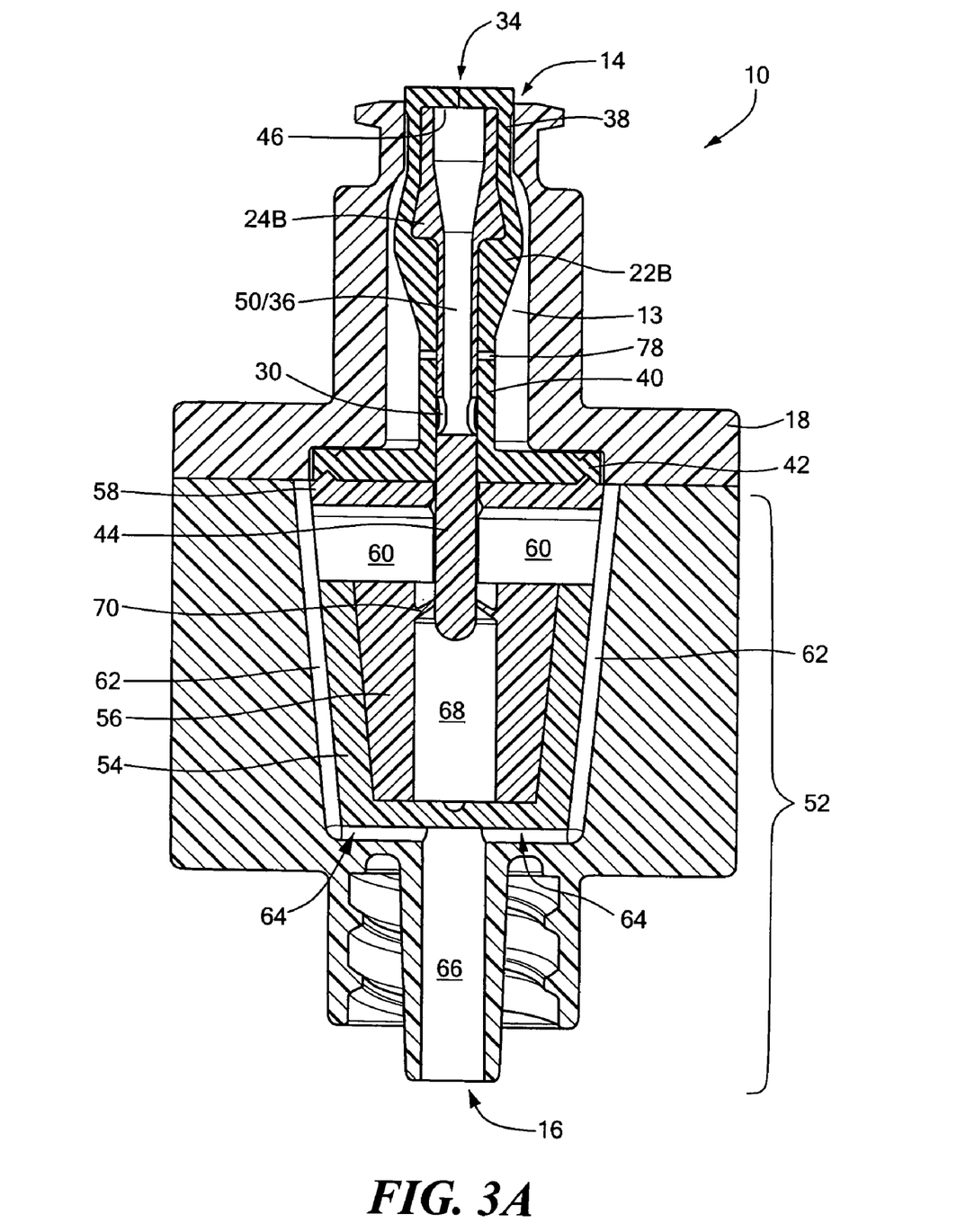
FIGS. 3A and 3B schematically show cross-sectional view of the valve shown in FIG. 1 in a closed mode and configured in accordance with a second embodiment of the invention.
Figure 3B:
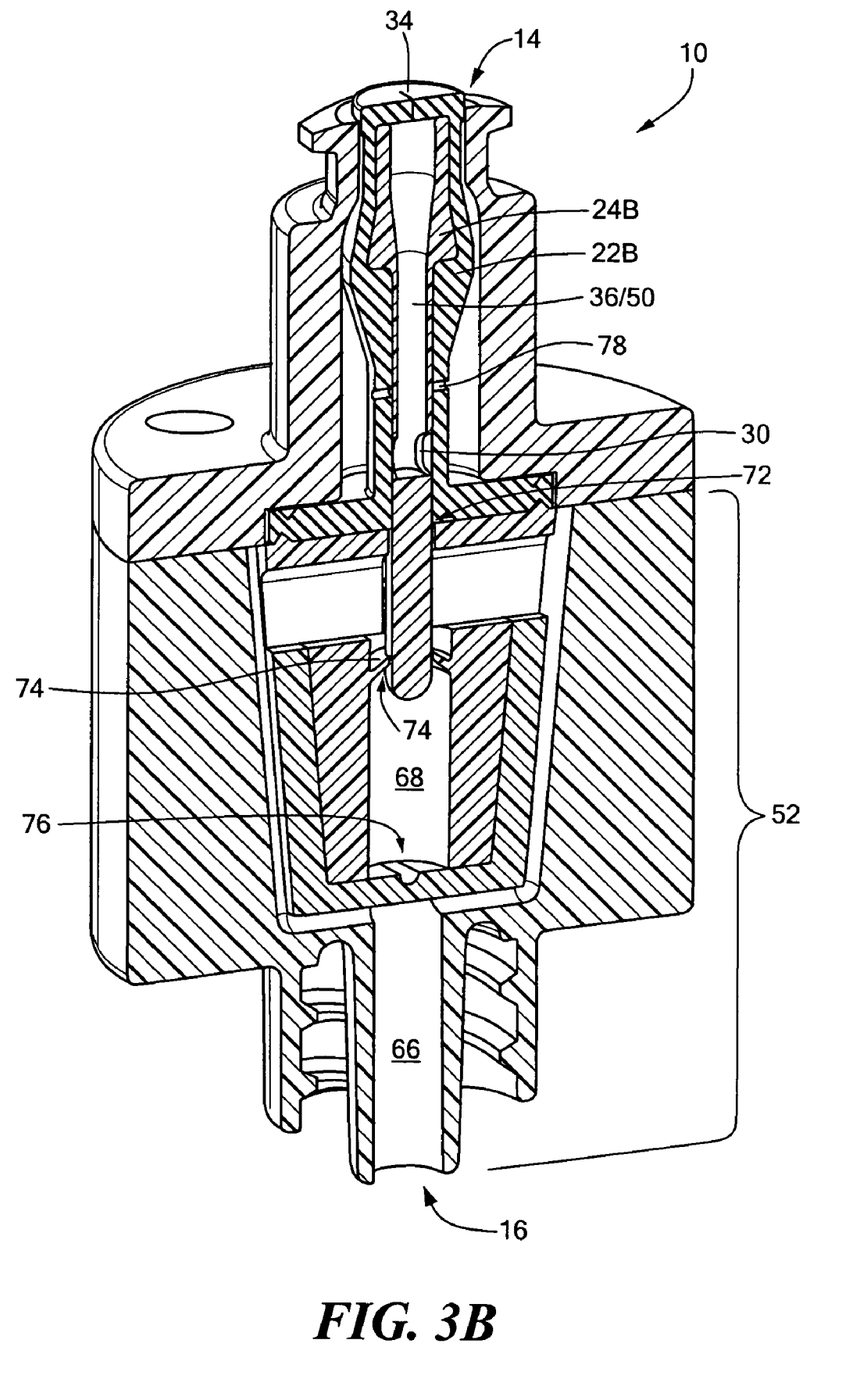

FIGS. 3A and 3B schematically show cross-sectional views of the valve 10 configured in accordance with a second embodiment of the invention. Specifically, in this and related embodiments, the valve 10 is configured to have a neutral drawback. Ideally, a neutral drawback has 0.0 microliters of positive or negative drawback. As suggested above, however, in practice, a neutral drawback actually can have a very slight positive or negative drawback (i.e., a manufacturing tolerance), such as a drawback on the order of positive or negative one microliter, or less. For anticipated applications, any such drawback is considered to be negligible.

In a manner similar to other embodiments, the valve 10 in this embodiment has a housing 12 with inlet and outlet housing portions 18 and 20 forming an interior 13, and a plurality of components forming a valve mechanism within the interior 13. The components forming the valve mechanism include a substantially rigid and longitudinally movable cannula 24B having an internal bore 36 making up a part of the internal valve flow path, and a stretchable and compressible gland 22B secured between the inlet and outlet housing portions 18 and 20 for both biasing and sealing the cannula 24B.

In illustrative embodiments, the gland 22B is formed from an elastomeric material, such as silicone or rubber. Other materials having similar properties may be used, however, so long as they can perform the functions discussed herein. The gland 22B has several cooperating sections for controlling fluid flow through the valve 10 while substantially eliminating fluid drawback. Namely, the gland 22B has a proximal section 38 having a slit 34, a central section 40 tightly circumscribing the cannula 24B and having optional vents 78, and an attachment section 42 for securing the gland 22B within the valve 10.

The cannula 24B may be any tube or other substantially rigid apparatus, such as a hollow needle, that may be configured to perform the discussed functions. As discussed below, the cannula 24B can be formed from a sufficiently rigid material that substantially prevents its body from bending during use. For example, among other things, the cannula 24B may be formed from a liquid crystal polymer, an elastomer, polycarbonate, polyethylene or polypropylene.

In the embodiment shown in FIGS. 3A and 3B, the bore 36 extends from the proximal section 38 of the gland 22B to a longitudinally extending solid cannula portion 44. Specifically, the bore 36 extends from an opening 46 at its proximal end, to holes 30 in its side. The solid cannula portion 44 is distal of the holes 30. When in the closed mode, the gland 22B normally occludes the holes 30 by means of an interference fit (e.g., on the order of 5-10 thousands of an inch). In addition, the proximal section 38 of the gland 22B normally occludes the opening 46 at the proximal end of the cannula 24B when in the closed mode. Accordingly, the valve 10 is considered to have a proximal seal formed by the slit proximal section 38 of the gland 22B, and an interior seal formed by the interference fit of the gland 22B about the portion of the cannula 24B having the holes 30.

When the valve 10 is in the closed mode/position, the proximal section 38 of the gland 22B is flush with, or extends slightly above, the exterior inlet face of the housing 12 (see, for example, FIGS. 3A and 3B). The proximal section 38 and the exterior inlet face thus present a swabbable surface. In other words, the proximal section 38 and the exterior inlet face may be easily wiped clean by any conventional means, such as with an alcohol swab. Valves having swabbable surfaces are known in the art as "swabbable valves." In other embodiments, however, the valve 10 is not a swabbable valve.

In accordance with illustrative embodiments of the invention, the flow path is configured to have a neutral drawback. To that end, the flow path is considered to have a movable first portion (i.e., a "dynamic portion 50," which in this embodiment comprises the bore 36), and a static second portion (a "static portion 52") that cooperates with the dynamic portion 50 to provide the neutral drawback. Longitudinal movement of the cannula 24B relative to the static portion 52 controls the mode of the valve 10.

One or more components cooperate to form the static portion 52 of the flow path. Among other things, those components may be integrated into the housing 12 (e.g., by conventional injection molding processes), or be separate parts inserted into the housing interior 13. For example, when separate parts, the components may include a basket 54 containing an insert 56, and a spacer 58 for forming at least one wall of the static portion 52 of the flow path. The basket 54, insert 56, and spacer 58 illustratively are formed from the same material as the housing 12 (e.g., a hard plastic). Discussion of such components, however, is exemplary and not intended to limit the scope of various embodiments.

In either case, the static portion 52 of the flow path includes a radially extending portion (formed by radially extending walls and referred to as the "first radial path 60") that terminates at a tapered wall. The tapered wall may form a substantially longitudinally directed flow path 62 that terminates in a more distally located radially extending flow path portion ("second radial path 64"). The flow path continues to a longitudinally directed distal flow path 66 that terminates at the distal port 16 of the valve 10. During and between both modes of use, the cannula 24B is considered to meet at/form a substantially consistently sized boundary with at least part of the static portion 52 of the flow path.

To facilitate cannula movement, the interior 13 of the valve 10 forms a vented receiving chamber 68 for receiving the distal end of the cannula 24B during and between all modes of use of the valve 10. The receiving chamber 68, however, is outside of the flow path and thus, has a substantially nonmovable ring seal 70 that separates its interior from the flow path. In illustrative embodiments, the ring seal 70 is upwardly tapered and formed from a material having some pliability, and yet does not move a sufficient amount to displace a non-negligible fluid volume. For example, the ring seal 70 may be formed from an elastomeric or semi-rigid material (e.g., polyethylene or polypropylene), which may be applied in a two-shot molding process. In alternative embodiments, the ring seal 70 may be formed from the same material as that used to form the housing 12. Accordingly, the ring seal 70 seals against the movable cannula 24B to isolate the receiving chamber 68 from the flow path. The ring seal 70 therefore also may be considered to form a boundary with the static portion 52 of the flow path.

In illustrative embodiments, the interior 13 of the housing 12 contains a plurality of additional flow paths that are configured to be substantially identical to that discussed above with regard to the static portion 52 of the flow path. For example, FIGS. 3A and 3B show at least two flow paths that each are configured as discussed above and together form the static portion 52 of the flow path. In fact, the respective first radially extending paths of both paths of the embodiment shown in FIGS. 3A and 3B may be considered to form a single first radially extending path through which the cannula 24B extends. Specifically, the cannula 24B extends from a proximally located boundary 72 (of the single radially extending flow path) to a distally located boundary 74 during and between both modes of use of the valve 10.

In addition to not moving relative to the housing 12, the static portion 52 of the flow path also maintains a substantially static shape during and between all modes of use. In other words, the shape of the static portion 52 does not change during and between all modes of use. The walls also neither expand nor contract. Movement of the cannula 24B should not be considered to affect the shape of the static portion 52.

Figure 4A:
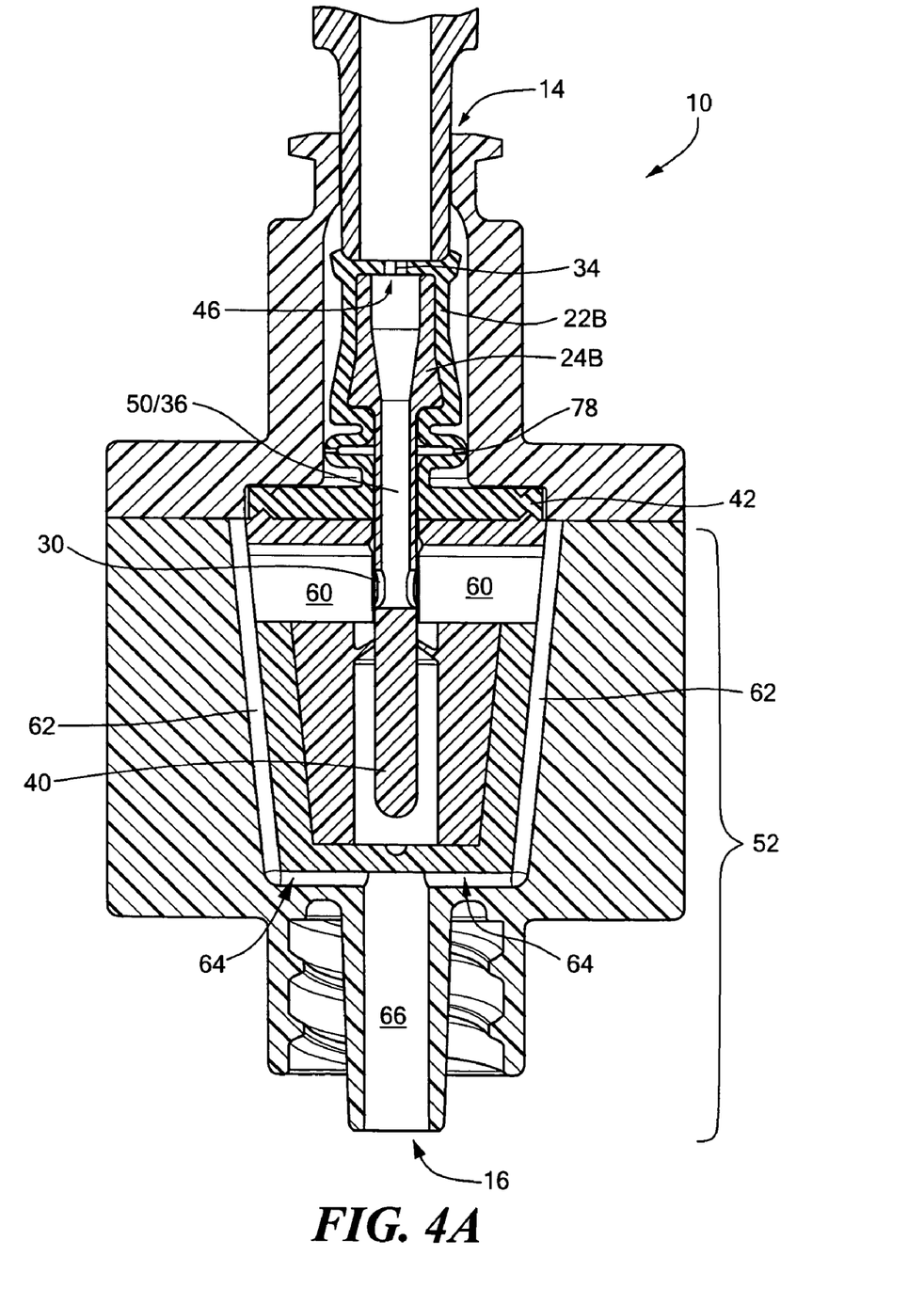
FIGS. 4A and 4B schematically show cross-sectional view of the valve embodiment shown in FIGS. 3A and 3B in an open mode.
Figure 4B:
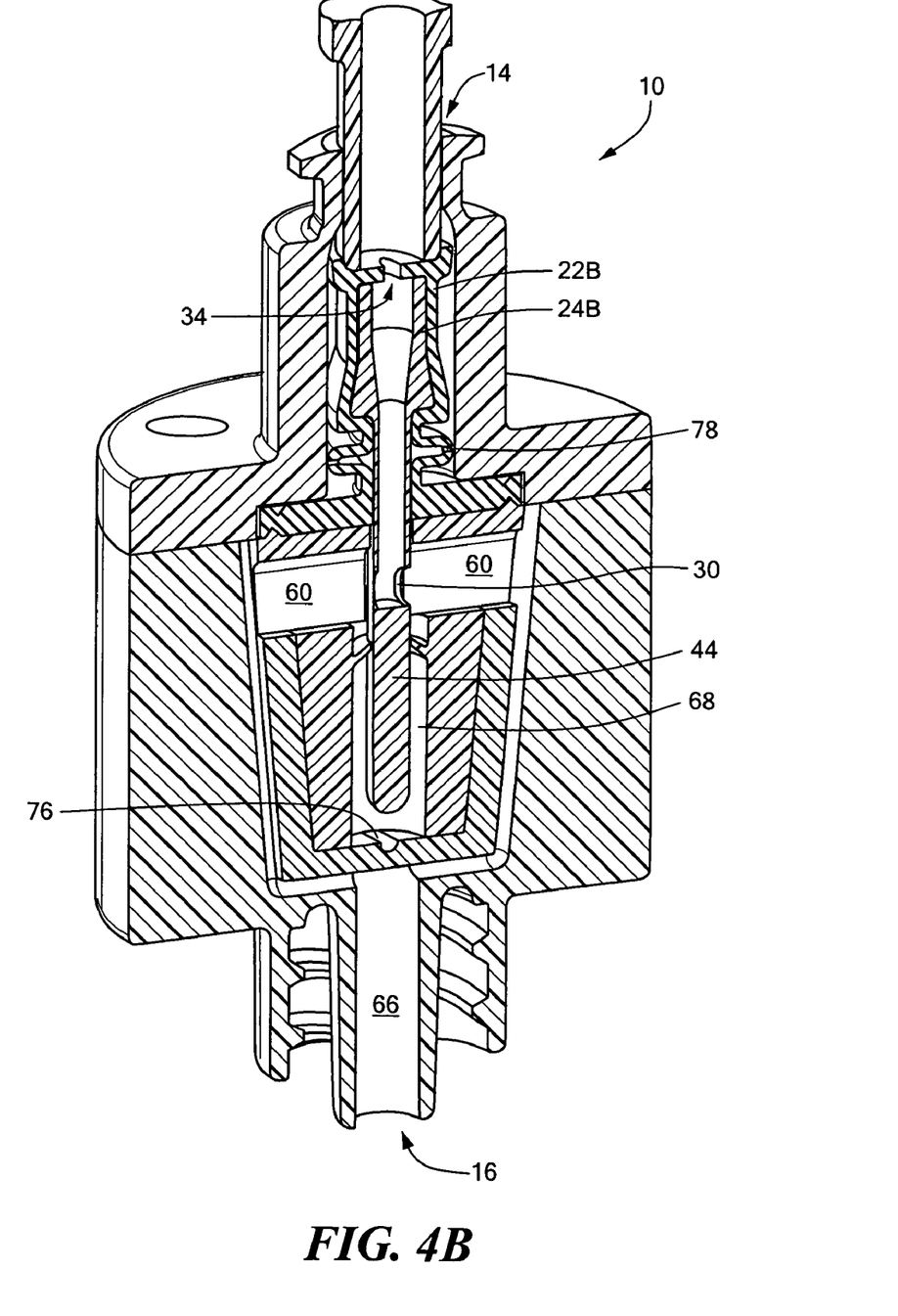

As shown in FIGS. 4A and 4B, insertion of a nozzle (e.g., an ANSI/ISO standard luer) into the proximal port 14 forces the gland 22B and cannula 24B to move distally to an open position. As shown, this causes the cannula holes 30 to move longitudinally away from occluding contact with the gland 22B at about the same time. In addition, a combination of forces cooperate to open the slit 34. Among those forces is the response of the gland 22B to the longitudinal force of the nozzle. In addition, the inner diameter of the housing 12 is smaller near the proximal port 14. After tapering for a relatively short distance, however, the inner diameter of the housing 12 expands significantly, thus permitting the proximal section 38 of the gland 22B to more freely open the slit 34.

Figure 5:
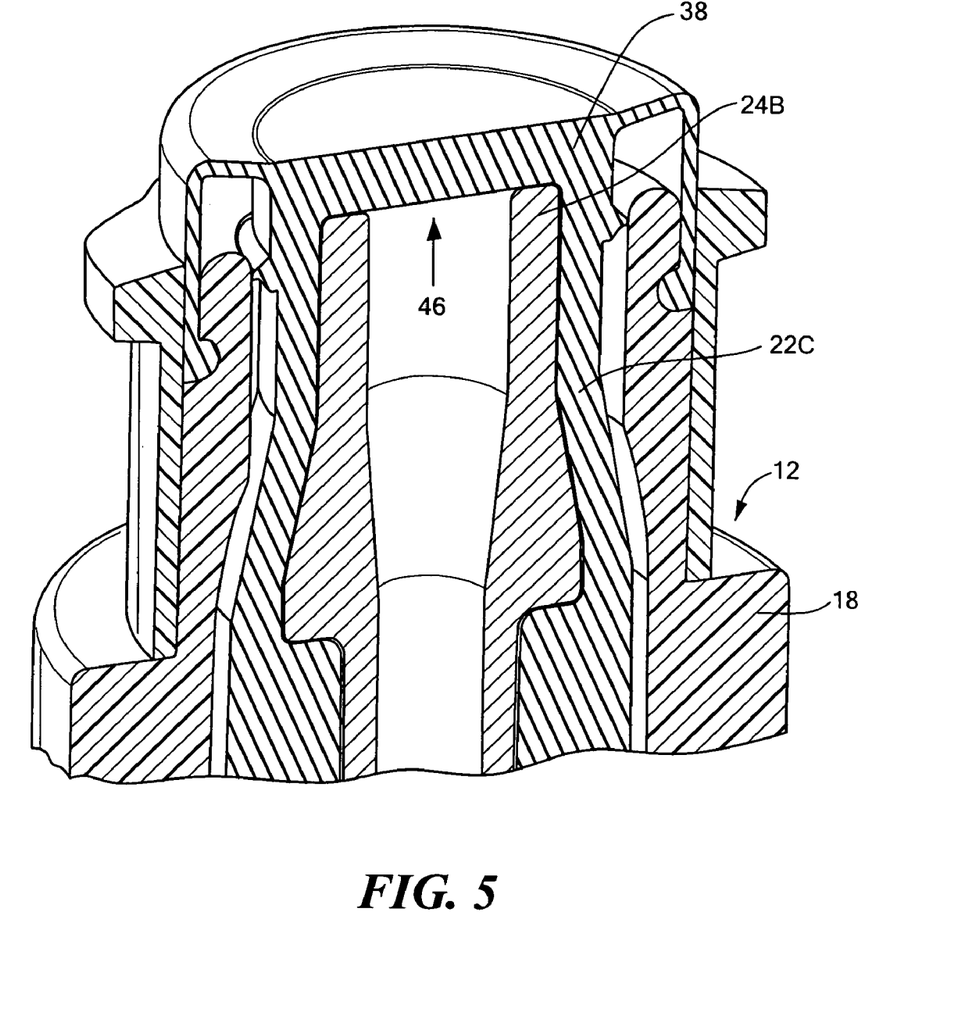
FIG. 5 schematically shows an alternative embodiment of the proximal end of the valve shown in FIG. 1.

FIG. 5 schematically shows an alternative embodiment of the proximal end of the valve 10, in which the proximal section 38 of the gland 22B extends radially outwardly and about the outer surface of the proximal port 14. In essence, such a gland 22B forms a type of "trampoline" about the proximal port 14. Such an embodiment effectively forms a proximal spring that provides an additional radially directed opening force for the slit 34. In addition, the spring also acts as a diaphragm for preventing inadvertent leakage of fluid from the nozzle in the space between the gland 22B and the housing 12 (i.e., the interstitial space). This seal is not necessary to keep such fluid from the flow path, however, because the attachment section 38 of the gland 22B acts as a fluid barrier.

When in the open position, the formerly non-contiguous flow path becomes contiguous between the open proximal end 46 of the cannula 24B and the distal port 16 of the valve 10. More specifically, the flow path within the interior 13 of the housing 12 is considered to be formed through the following sequential portions:

The proximal opening 46 of the cannula 24B,
The bore 36 in the cannula 24B,
Through the cannula holes 30,
The first radial path 60 of the static portion 52,
The longitudinally directed flow path 62,
The second radial path 64 of the static portion 52,
The distal flow path 66, and
Through the distal port 16.

More specifically, to open the valve, the nozzle applies a distally directed force directly against the top of the proximal section 38 of the gland 22B. When the distally directed force exceeds the proximally directed biasing force of the gland 22B, the cannula 24B and gland 22B begin translating distally. Consequently, the central section 40 of the gland 22B begins to deform, such as in the convoluted manner shown in FIG. 4A. It is anticipated, however, that the gland 22B may deform in some other way, such as by bulging radially or compressing without bulging or convoluting, while maintaining contact against the cannula wall. It should be noted that the cannula holes 30 should remain occluded until they extend distally of the gland 22B.

Distal movement of the cannula 24B also forces air from the receiving chamber 68 through a chamber vent 76. Accordingly, air in the receiving chamber 68 should not present an additional impedance for opening the valve. Moreover, gland vents 78 prevent the gland 22B from forming a vacuum that could potentially draw fluid from a fluid path through the cannula holes 30. Of course, the gland vents 78 are positioned so that they do not interfere with the role of the central section 40 of the gland 22B in occluding the cannula holes 30. In alternative embodiments, other means may be used to ensure that fluid does not escape from the flow path and into the space between the gland 22B and the cannula 24B. For example, an o-ring may be secured about the gland 22B to fill the space between the gland 22B and inner wall of the housing 12. Such means should further ensure the interference fit of the gland 22B. As a second example, the valve also may have additional material at the distal end of the gland 22B to provide additional sealing functionality.

As it translates distally, the cannula 24B does not displace any additional volume in the flow path. In particular, as the cannula 24B translates along the boundary of the first radial path 60 (of the static portion 52 of the flow path), it does not positively or negatively displace fluid within the priming volume of the static portion 52. Instead, it displaces a constant amount of the interior of the static portion 52 of the flow path; namely, the volume in FIGS. 3A, 3B, 4A, and 4B between the two first radial flow paths 60. Accordingly, although the cannula 24B translates into this area, an equal amount of the cannula 24B translates from this area and into the receiving chamber 68. The internal volume of the static portion 52 therefore remains static, thus not inducing a positive or negative vacuum at the distal port 16.

At some point during the opening stroke of the valve, the cannula holes 30 break through their occluding contact with the gland 22B and contact the second portion of the flow path (i.e., at the first radial portion). Those skilled in the art should understand that this movement should have no more than a negligible impact on the volume of the flow path because it simply joins two constant volume paths (i.e., the dynamic and static portions 50 and 52 of the flow path). In particular, during and between all modes of use, the bore 36 has a constant bore volume, while the static portion 52 also has a constant second volume. Distal movement of the bore 36 simply directly fluidly connects these two volumes. Accordingly, when in the open mode, the cannula holes 30 essentially are positioned along/form the boundary of the static portion 52 of the flow path. The cannula holes 30 thus also may be considered to "bound" the second portion of the flow path.

Removal of the nozzle similarly enables the restoring force of the gland 22B to force the cannula 24B proximally. Because the internal volumes and/or shape of the flow path remain substantially static, there should be no positive or negative pressure formed at the distal port 16 (despite its relative movement). In particular, the total volume of the flow path is substantially the same in both the open mode and closed mode. In fact, in illustrative embodiments, the total volume of the flow path remains substantially constant during and between both modes. As noted above, this result is due largely to the shifting, substantially constant volumes and static shapes/walls of the two portions of the flow path. Accordingly, the distal port 16 should have a neutral drawback both when inserting a nozzle into, and removing a nozzle from, the proximal port 14.

Although not necessary, a line leading to the valve also can be clamped while a nozzle is connected or withdrawn from the valve 10. Unlike various prior art valves, however, the valve 10 still should return to its closed, swabbable position because, among other reasons, it produces neither a negative nor positive vacuum at the distal port 16. Of course, clamping the line should be unnecessary when using the valve 10.

Figure 6:
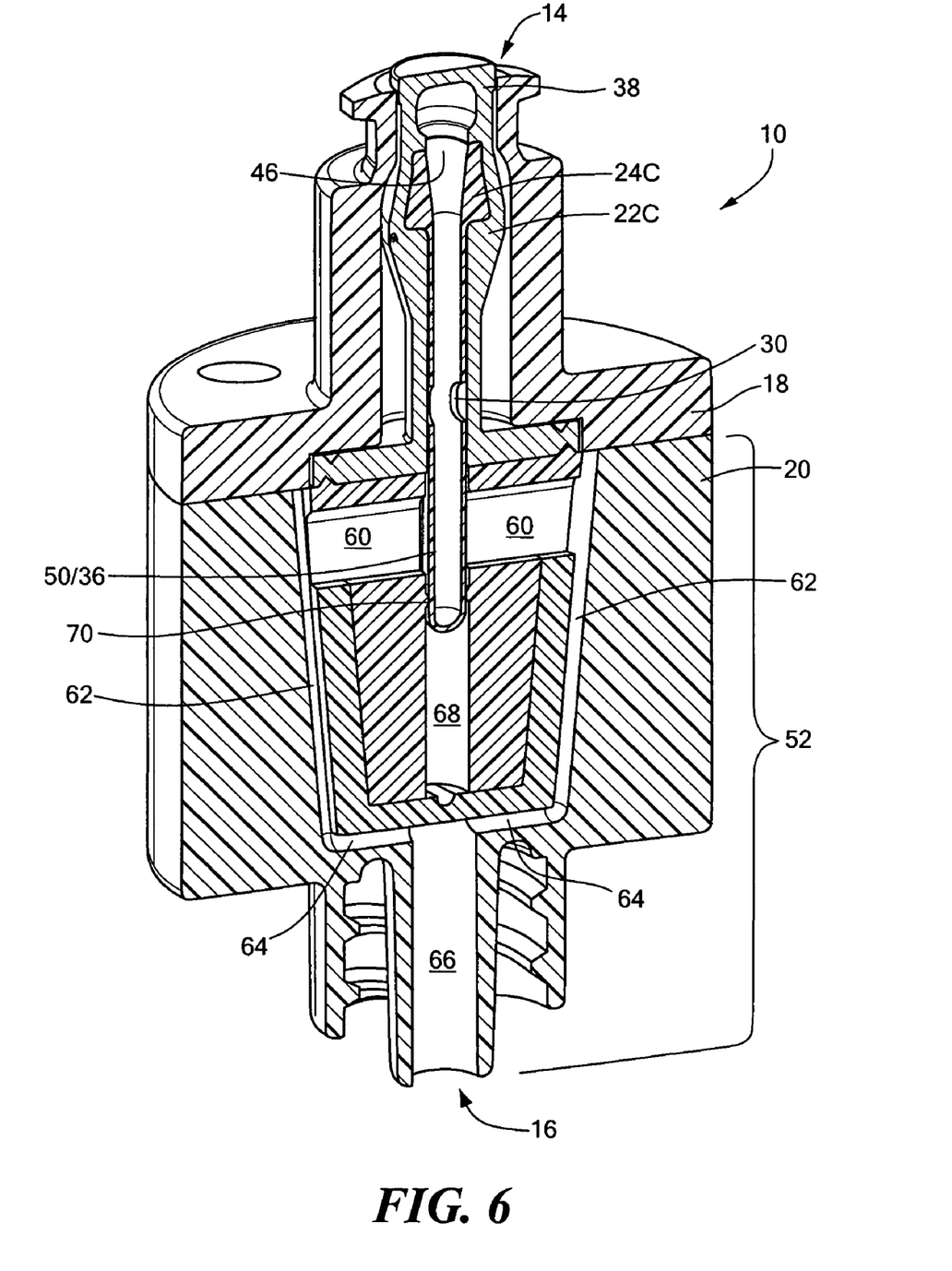
FIG. 6 schematically shows a cross-sectional view of the medical valve shown in FIG. 1 configured in accordance with a third embodiment of the invention.

FIG. 6 schematically shows another embodiment of the invention, in which the bore 36 extends substantially along the entire length of the cannula 24C. In addition, the flow path of this embodiment also has a small portion with deformable (i.e., non-static) walls formed by the gland 22C. Moreover, the ring seal 70 of this embodiment is not tapered proximally. In this embodiment, however, the ring seal 70 may be flexible enough to compensate for volume changes in other portions of the flow path, if any such portions exist. Those skilled in the art can selectively combine these and features of other embodiments to form a valve having the desired functionality.

Although the above discussion discloses various exemplary embodiments of the invention, it should be apparent that those skilled in the art can make various modifications that will achieve some of the advantages of the invention without departing from the true scope of the invention.

What is claimed is:

1. A medical valve having an open mode that permits fluid flow, and a closed mode that prevents fluid flow, the medical valve comprising:
    a housing forming an interior;
    a valve mechanism within the interior, the valve mechanism having a substantially rigid translating member with a bore and an elastomeric member sealing the bore in the closed mode,
    the interior of the housing having a flow path that includes at least a portion of the bore of the translating member,
    the flow path having an open mode volume when the valve is in the open mode, the fluid path also having a closed mode volume when the valve is in the closed mode, the open mode volume being substantially equal to the closed mode volume, and movement of the translating member causing substantially no volumetric change within any part of the flow path when the valve transitions between the open and closed modes.

2. The medical valve as defined by claim 1 wherein the flow path has a volume that remains substantially constant as the valve transitions between the open mode and the closed mode.

3. The medical valve as defined by claim 1 wherein the flow path comprises the at least a portion of the bore and a second portion, the translating member extending through the second portion of the flow path.

4. The medical valve as defined by claim 1 wherein the interior also includes a receiving chamber that is outside of the flow path, the translating member extending into the receiving chamber when the valve is in the closed mode.

5. The medical valve as defined by claim 1 wherein the flow path comprises the at least a portion of the bore and a second portion, the second portion having a substantially constant volume as the valve transitions between modes.

6. The medical valve as defined by claim 1 wherein the translating member has a substantially static shape as the valve transitions between the open mode and the closed mode.

7. The medical valve as defined by claim 1 wherein the valve substantially has neither a positive push nor a drawback when the valve transitions from the open mode to the closed mode.

8. The medical valve as defined by claim 1 wherein the valve substantially has neither a positive push nor a drawback when the valve transitions from the closed mode to the open mode.

9. The medical valve as defined by claim 1 wherein the translating member includes a cannula.

10. The medical valve as defined by claim 1 wherein the valve mechanism has a proximal section, the housing also having a distal port, the flow path extending from the proximal section of the valve mechanism to the distal port.

11. A medical valve having an open mode that permits fluid flow, and a closed mode that prevents fluid flow, the medical valve comprising:
    a housing forming an interior having a proximal port and a distal port, the interior forming a flow path between the proximal port and the distal port,
    a translating member having a bore, the translating member being longitudinally movable within the interior, the flow path comprising the bore and a second portion,
    the translating member bounding the second portion of the flow path, the flow path maintaining a substantially constant volume when the valve transitions between the open mode and the closed mode; and
    an elastomeric member normally biasing the translating member to close the valve, the elastomeric member sealing the bore when in the closed mode.

12. The medical valve as defined by claim 11 wherein the second portion remains substantially stationary within the interior when the valve transitions between the open and closed modes.

13. The medical valve as defined by claim 11 wherein the bore maintains a substantially constant volume between the open and closed modes.

14. The medical valve as defined by claim 11 wherein movement of the translating member causes substantially no volumetric change within any part of the flow path when the valve transitions between the open and closed modes.

15. The medical valve as defined by claim 11 wherein the elastomeric member is within the interior, the elastomeric member preventing fluid flow through the bore when the valve is in the closed mode.

16. The medical valve as defined by claim 15 wherein the bore has at least two longitudinally spaced openings, the elastomeric member occluding the at least two longitudinally spaced openings when the valve is in the closed mode.

17. The medical valve as defined by claim 11 further comprising a valve mechanism, the valve mechanism including the translating member and the elastomeric member, the valve mechanism being substantially flush with or extending proximally from the proximal port when the valve is in the closed mode.

18. The medical valve as defined by claim 11 wherein the translating member includes a tube.

19. The medical valve as defined by claim 18 wherein the tube has a side wall forming an opening, the side wall terminating at a closed distal end, the opening being occluded when the valve is in the closed mode.

20. The medical valve as defined by claim 11 wherein the interior has a receiving chamber outside the flow path, the translating member being at least partly within the receiving chamber when the valve is in the closed mode.

21. The medical valve as defined by claim 11 wherein the second portion of the flow path has a part with a first boundary and a second boundary, the translating member extending at least from the first boundary to the second boundary.

22. The medical valve as defined by claim 11 wherein the second portion of the flow path has at least one radially extending wall.

23. The medical valve as defined by claim 11 wherein the distal port substantially has neither a positive push nor a drawback when the valve transitions from the open mode to the closed mode.

24. The medical valve as defined by claim 11 wherein the translating member bounds the second portion of the flow path in both the closed mode and in the open mode.

25. The medical valve as defined by claim 11 wherein the second portion of the flow path remains substantially static as the valve transitions between the open mode and the closed mode.

26. A method of controlling fluid flow through a valve having an interior, the valve having an open mode that permits fluid flow, and a closed mode that prevents fluid flow, the method comprising:
   forming a flow path within the interior, the flow path comprising a first portion and a second portion;
   inserting a nozzle into the valve; and
   longitudinally moving the first portion relative to the second portion to change the mode of the valve, each of the first portion and the second portion having a substantially static shape when the valve transitions between the open mode and the closed mode, the nozzle longitudinally moving the first portion relative to the second portion as the nozzle is inserted into the valve, the valve having an elastomeric member that seals the first portion of the flow path when in the closed mode.

27. The method as defined by claim 26 wherein the first portion has a substantially constant volume when the valve transitions between the open mode and the closed mode, the second portion having a substantially constant volume when the valve transitions between the open mode in the closed mode.

28. The method as defined by claim 26 wherein the valve has a distal port substantially having neither a positive push nor a drawback when the first portion longitudinally moves relative to second portion.

29. The method as defined by claim 26 wherein the flow path has a substantially constant volume when the first portion longitudinally moves relative the second portion.

30. The method as defined by claim 26 wherein a first component forms the first portion, the first component displacing a displacement volume within the second portion, the displacement volume remaining substantially constant as the valve transitions between the open mode and the closed mode.

31. The method as defined by claim 26 wherein the first portion bounds the second portion in both the open mode and the closed mode.

32. The method as defined by claim 26 wherein a line is connected to the valve, the first portion of the flow path being in a closed position when in the closed mode, the method further comprising:
   clamping the line when in the open mode, the first portion of the flow path returning to the closed position when the line is clamped.

33. A medical valve having an open mode that permits fluid flow, and a closed mode that prevents fluid flow, the medical valve comprising:
   a housing having a distal port and an interior,
   a valve mechanism within the interior, the valve mechanism having an elastomeric sealing member,
   the interior having components forming a flow path extending from the elastomeric sealing member and terminating at the distal port, the elastomeric sealing member cooperating with at least one of the components to selectively open and close the valve, the elastomeric sealing member normally biasing at least one of the components to close the valve, and
   the components each maintaining substantially constant shapes as the valve transitions between the open mode and the closed mode,
   the distal port substantially having neither a positive push nor a drawback when the valve transitions from the open mode to the closed mode.

34. The medical valve as defined by claim 33 wherein the distal port substantially has neither a positive push nor a drawback when the valve transitions from the closed mode to the open mode.

35. The medical valve as defined by claim 33 wherein the components include:
   a first component forming a first portion of the flow path; and
   a second component forming a second portion of the flow path,
   the first component moving relative to the second component as the valve transitions from the open mode to the closed mode.

36. The medical valve as defined by claim 35 wherein the first portion and second portion of the flow path are not in fluid communication during the closed mode.

37. The medical valve as defined by claim 33 wherein the components comprise a translating member having a bore, the flow path comprising the bore and a second portion, the translating member bounding the second portion of the flow path during both the open mode and closed mode.

38. The medical valve as defined by claim 33 wherein the entire flow path maintains a substantially constant volume as the valve transitions from the open mode to the closed mode.

39. The medical valve as defined by claim 33 wherein the components define the entire flow path through the valve.

40. The medical valve as defined by claim 33 wherein the components comprise at least one of a translating member and an interior contour of the housing.

41. A medical valve having an open mode that permits fluid flow, and a closed mode that prevents fluid flow, the medical valve comprising:

a housing forming an interior;

means for controlling fluid flow within the interior, the controlling means having a translating means with a bore and an elastomeric member sealing the bore in the closed mode, the interior of the housing having a flow path that includes at least a portion of the bore of the translating means, the flow path having an open mode volume when the valve is in the open mode, the fluid path also having a closed mode volume when the valve is in the closed mode, the open mode volume being substantially equal to the closed mode volume, and movement of the translating means causing substantially no volumetric change within any part of the flow path when the valve transitions between the open and closed modes.

42. The medical valve as defined by claim 41 wherein the translating means comprises a translating member.

43. The medical valve as defined by claim 41 wherein the controlling means comprises a valve mechanism.

44. The medical valve as defined by claim 41 wherein the flow path has a volume that remains substantially constant as the valve transitions between the open mode and the closed mode.

45. The medical valve as defined by claim 41 wherein the flow path comprises the at least a portion of the bore and a second portion, the translating means extending through the second portion of the flow path.

46. The medical valve as defined by claim 41 wherein the interior also includes means for receiving the translating means, the receiving means being outside of the flow path, the translating means extending into the receiving means when the valve is in the closed mode.

47. The medical valve as defined by claim 41 wherein the translating means has a substantially static shape as the valve transitions between the open mode and the closed mode.

48. The medical valve as defined by claim 41 wherein the valve substantially has neither a positive push nor a drawback when the valve transitions from the open mode to the closed mode.

49. The medical valve as defined by claim 41 wherein the valve substantially has neither a positive push nor a drawback when the valve transitions from the closed mode to the open mode.

50. The medical valve as defined by claim 41 wherein the interior housing has a receiving chamber for receiving the translating means, the receiving chamber having a tapered seal that seals the receiving chamber.

\* \* \* \* \*